United States Patent [19]

Seaton

[11] Patent Number: 4,813,873

[45] Date of Patent: Mar. 21, 1989

[54] DENTAL PROSTHETIC STRUCTURES AND CONNECTORS FOR USE IN SUCH PROSTHETIC STRUCTURES

[76] Inventor: Peter Seaton, 3, Trinity Street, Dorchester, Dorset, DT1 1TT, United Kingdom

[21] Appl. No.: 12,821
[22] PCT Filed: Jun. 12, 1986
[86] PCT No.: PCT/GB86/00336
§ 371 Date: Feb. 4, 1987
§ 102(e) Date: Feb. 4, 1987
[87] PCT Pub. No.: WO86/07251
PCT Pub. Date: Dec. 18, 1986

[30] Foreign Application Priority Data

Jun. 12, 1985 [GB] United Kingdom ............... 8514897
Oct. 21, 1985 [GB] United Kingdom ............... 8525920

[51] Int. Cl.⁴ ..................................... A61C 13/225
[52] U.S. Cl. ..................................... 433/181; 433/169; 433/177; 433/182
[58] Field of Search ............... 433/181, 182, 183, 180, 433/169, 177, 178, 191, 192, 193, 194, 195, 196

[56] References Cited

U.S. PATENT DOCUMENTS

| | | | |
|---|---|---|---|
| 1,614,325 | 1/1927 | Stoeffler | 433/177 |
| 1,664,433 | 4/1928 | Seabrook | 433/183 |
| 1,698,259 | 1/1929 | Craig | 433/181 |
| 1,921,613 | 8/1933 | Freedman | 433/169 |
| 2,350,196 | 5/1944 | Saffir | 433/191 |
| 2,491,581 | 12/1949 | Reichner | 433/191 |
| 2,571,931 | 10/1951 | Noyes | 433/169 |
| 2,668,353 | 2/1954 | Quellman | 433/177 |
| 2,705,366 | 4/1955 | Van Dyk | 433/182 |
| 3,019,528 | 2/1962 | De Pietro | 433/169 |
| 4,362,509 | 12/1982 | Sulc | 433/181 |
| 4,431,415 | 2/1984 | Tigani | 433/172 |
| 4,472,142 | 9/1984 | Gedzelman | 433/170 |
| 4,661,068 | 4/1987 | Harrison et al. | 433/181 |

FOREIGN PATENT DOCUMENTS

| | | | |
|---|---|---|---|
| 693561 | 11/1930 | France | 433/181 |
| 984623 | 7/1951 | France | 433/177 |
| 995727 | 12/1951 | France | 433/181 |
| 491643 | 7/1970 | Switzerland | 433/177 |

Primary Examiner—John J. Wilson
Attorney, Agent, or Firm—Marshall, O'Toole, Gerstein, Murray & Bicknell

[57] ABSTRACT

A dental prosthetic construction comprising a pontic and a connector limb attached to the pontic, the connector limb having a joint portion received in a socket of an abutment tooth to retain the pontic in an intended position, the joint portion of the connector limb being introduced into the socket in the abutment tooth along a path of insertion which is substantially parallel to the dental arch containing the abutment tooth and having bearing surfaces engaging bearing surfaces in the socket such that there is limited freedom of angular movement of the connector limb about the joint portion so as to permit stress-breaking relative movement between the connector limb and socket while maintaining contact between the connector limb and socket.

2 Claims, 8 Drawing Sheets

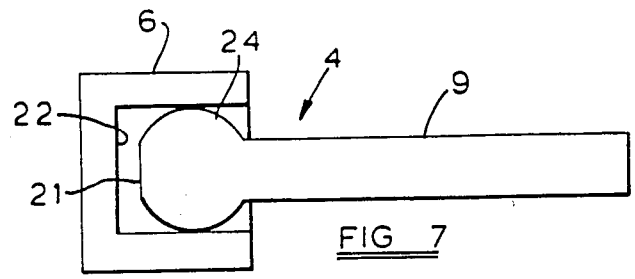
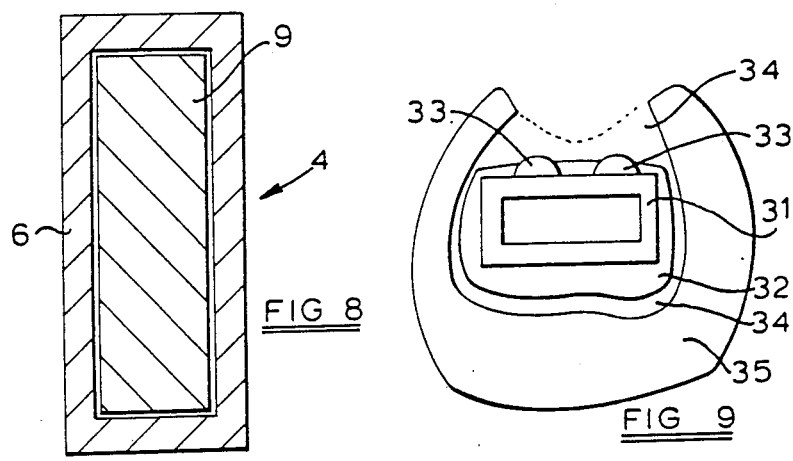
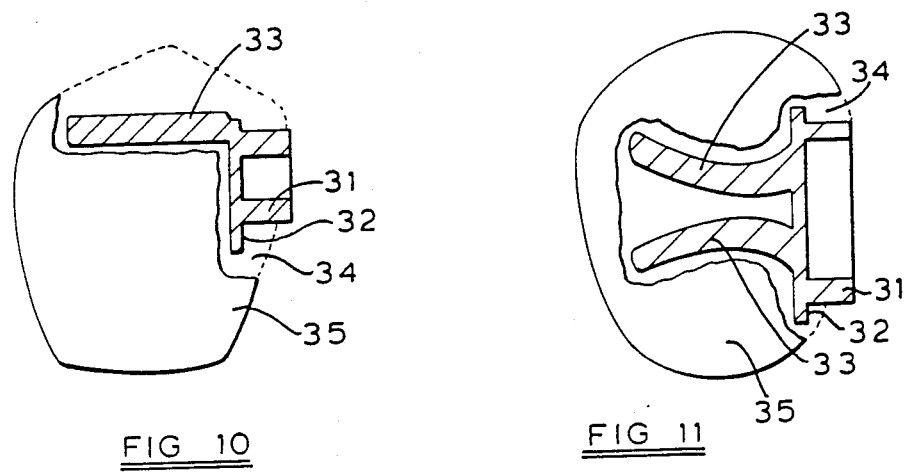

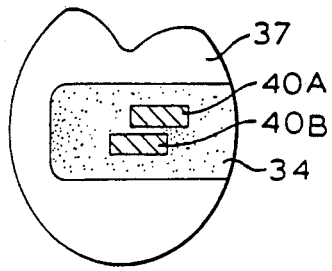
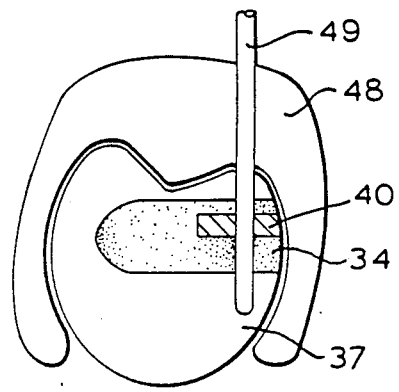
FIG 21  FIG 22
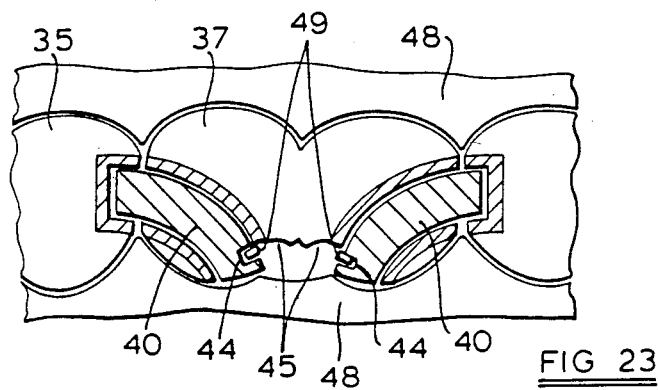
FIG 23
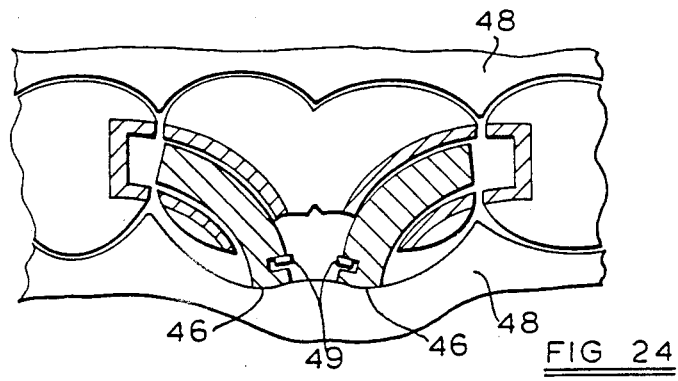
FIG 24

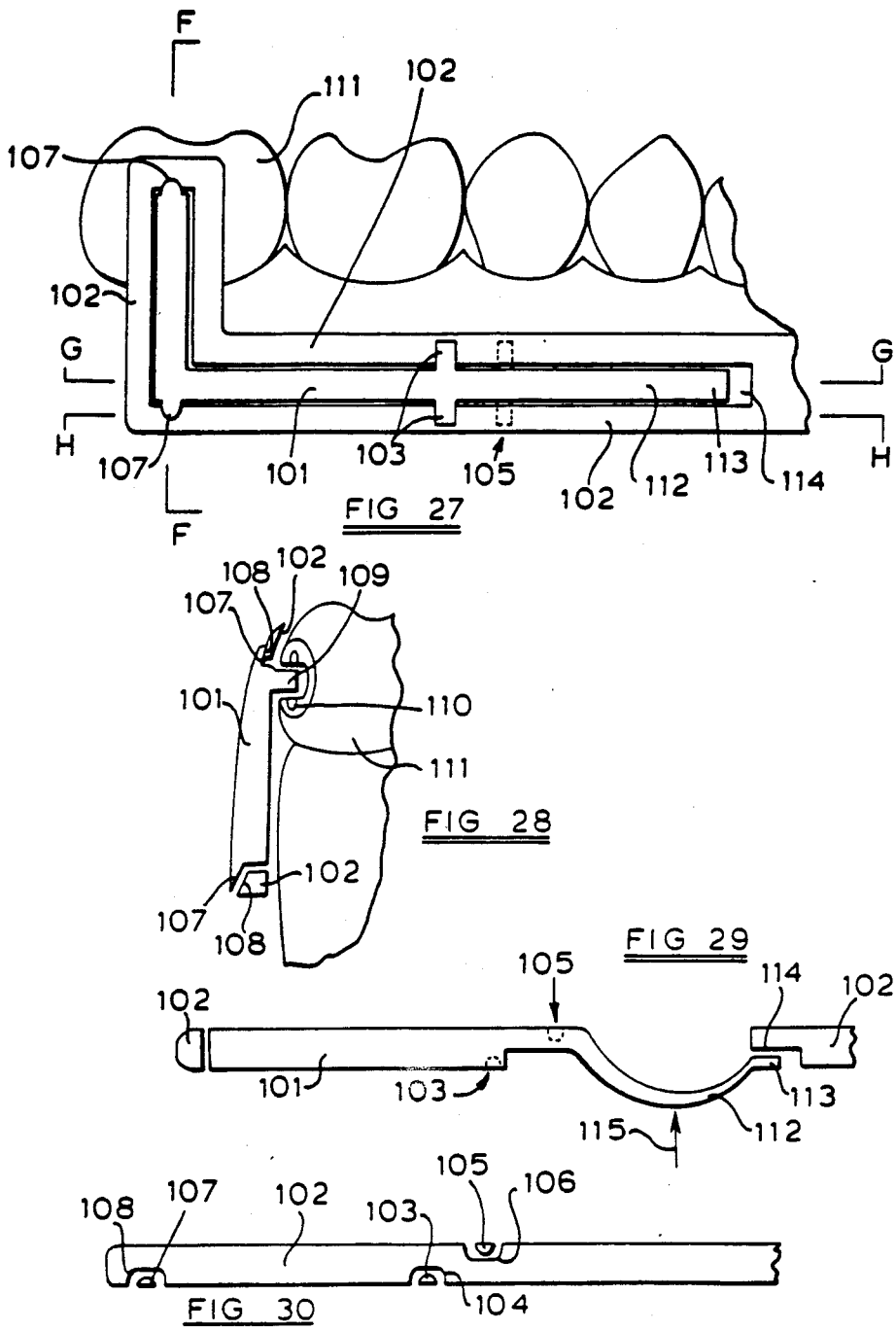

DENTAL PROSTHETIC STRUCTURES AND CONNECTORS FOR USE IN SUCH PROSTHETIC STRUCTURES

THIS INVENTION relates to improvements in or relating to the construction of both fixed and removable dental prosthetic structures, such as bridges and partial dentures.

A dental bridge comprises an artificial tooth or teeth, a so-called "pontic", supported on either side by a suitably prepared sound natural tooth called "an abutment tooth" in the art.

A number of different methods of providing a patient with a fixed dental bridge are currently in use, the majority of these methods involving a one-piece bridge construction made of a suitable dental material and incorporating the pontic and attachments for securing the pontic to the abutment teeth.

Providing the patient with a dental bridge by the known methods is achieved by first carrying out dental preparation work on the abutment teeth and then fabricating and installing the bridge construction consisting of the pontic and the appropriate attachments.

In one currently popular form of dental bridge, radical surgery is first carried out on both abutment teeth in order to form these into substantially parallel pillar-like structures which have a substantially constant cross-sectional area over a significant height. Once this surgery has been performed, casts are taken of the prepared abutment teeth for use in preparing cast sockets made of a dental metal for incorporating in the attachments of the dental bridge construction which is constructed as a unitary item consisting of the pontic and integrally cast attachments containing the metal sockets which fit accurately over the prepared abutment teeth. Installation of such a dental bridge construction is then performed by applying dental cement to the prepared abutment teeth and fitting the attachments of the dental bridge construction over the respective abutment teeth.

The preparation of the cast metal sockets and the unitary bridge construction including these involves a very high degree of skill, and additional difficulties are involved by the need for the attachments to be applicable to the prepared abutment teeth along parallel paths.

The bridge construction itself is necessarily made and assembled in a laboratory by a skilled technician, so that each bridge is individually made and is a unique piece of high precision work.

The unitary nature of the bridge construction described above also means that such bridge construction can be subjected in use to considerable bending moments and is liable to break or become detached under the forces encountered in the mouth.

Moreover, the surgery which is required to be performed on the abutment teeth is radical and may involve the destruction of considerable quantities of healthy tooth material.

A further disadvantage of the described known bridge construction is the fact that, in installing the bridge construction, the attachments are applied to the prepared and cemented abutment teeth in a path of application along with bi-directional forces commonly occur in the mouth. Consequently, the bridge construction is subjected to forces which tend to dislodge it and can be readily withdrawn along this path as a result of loss of adhesion between the bridge construction and the abutment teeth following shearing of the relatively thin layer of dental cement holding the abutment teeth and the bridge construction together.

It is an object of the present invention to provide an improved method of constructing a dental prosthetic structure and, to this end, there is provided a method of constructing a dental prosthetic structure, comprising providing an abutment tooth with a socket and retaining a pontic in an intended position by means of a connector limb attached to the pontic and having a joint portion received in the socket, the joint portion of the connector limb being introduced into the socket along a path of insertion which is substantially parallel to the dental arch containing the abutment tooth and fitting in the socket with a freedom of movement such as to permit stress-breaking relative movement between the connector limb and socket.

In another aspect, the invention provides a dental prosthetic construction comprising a pontic and a connector limb attached to or for attachment to the pontic, the connector limb having a joint portion for reception in a socket of an abutment tooth to retain the pontic in an intended position, the joint portion of the connector limb being introducible into the socket in the abutment tooth along a path of insertion which is substantially parallel to the dental arch containing the abutment tooth and fitting into the socket with a freedom of movement such as to permit stress-breaking relative movement between the connector limb and socket.

According to a further aspect, the invention provides a dental prosthetic connector for use in attaching a pontic to an abutment tooth, which connector has a first part including a limb and a second part defining a socket, the two connector parts having bearing surfaces at places of contact when engaged, which bearing surfaces are so arranged that there is complete freedom of movement of the limb within the socket along a path of insertion of the limb into the socket.

In another aspect, there is provided a dental prosthetic connector for use in attaching a pontic to an abutment tooth, which connector consists of a part including a limb constructed to fit a prepared socket-like cavity within the substance of the abutment tooth.

The invention further provides a dental prosthetic connector consisting entirely or in part of a limb which is arcuate in shape and movable along an axis thereof in a passage in the pontic in order to engage or disengage the connector.

In a further aspect of the present invention, there is provided a dental prosthetic construction comprising a pontic and a connector for attaching the pontic to an abutment tooth, the connector having a first part for attachment to the abutment tooth and a second part carried by the pontic, the connector parts fitting together so as to permit a degree of movement therebetween, in which construction one of the connector parts has retaining projections extending therefrom in more than one plane to assist in attaching the connector part to the pontic or abutment tooth.

The retaining projections of the one connector part need not be constructed from the same material as the rest of the connector part and could, with advantage, be capable of slight modification to suit particular installation requirements, for instance, by bending. In a preferred embodiment, the one part of the connector is the socket part.

In yet another aspect of the invention, there is provided a dental prosthetic contruction comprising a pontic and a connector for attaching the pontic to an abutment tooth, the connector having a first part for attachment to the abutment tooth and a second part carried by the pontic, the connector parts fitting together so as to permit a degree of movement therebetween, in which construction the part of the connector attached to the abutment tooth is attached to a restoration for fitting to the abutment tooth.

The term restoration is intended to cover laboratory-made items, such as a crown or inlay, and the connector part may be attached to the restoration by embedding in a matrix of filler material in an oversized cavity within the restoration, or may be attached by some other suitable means, such as welding, soldering, intrical casting, or the use of suitable bonding agents.

In accordance with another aspect of the present invention, there is provided a dental prosthetic construction comprising a pontic and a connector for attaching the pontic to an abutment tooth, the connector comprising a first part for attachment to the abutment totooth and a second portion carried by the pontic, the connector parts fitting together so as to permit a degree of movement therebetween, in which construction at least limited vertical movement of the pontic is permitted by the connector.

In the case of a socket and limb connector, such vertical movement is enabled by making the vertical dimension of the socket greater than the corresponding dimension of the joint portion of the limb.

In a preferred embodiment, both horizontal and vertical movement of the pontic is permitted by the connector. In the case of a socket and limb connector, this is achieved by making both the horizontal and vertical dimensions of the socket greater than the corresponding dimensions of the joint portion of the limb part.

In dental prosthetic constructions which permit vertical and/or horizontal movement of the pontic springs or magnets may be used to stablise the pontic in a resting position when chewing forces are not being applied, and also in order progressively to transfer a part of those forces to the abutment tooth, following movement of the joint portion of the limb within the socket.

In some embodiments which allow vertical or horizontal movement of the pontic and which employ socket and limb connectors, one or more of the walls of the socket may be omitted.

According to still another aspect of the present invention, there is provided a dental prosthetic construction comprising a pontic and a connector for attaching the pontic to an abutment tooth, the connector having a first portion attached to the pontic and a second portion carried by the pontic, the connector parts fitting together so as to permit a degree of movement therebetween, in which construction the first and second connector parts are disengagable from one another to permit removal of the pontic.

Such a construction enables the provision of removable constructions, such as bridges or partial dentures which can be inserted and removed at will.

In the case of a socket and limb connector, the limb part, or in certain circumstances the socket part, may be arranged to slide axially to withdraw the limb from the socket and enable removal of the pontic.

Where the limb part of the connector is slidable, the limb may be a straight member, guided for linear movement, preferably along the line of withdrawal from the socket. The limb could, however, slide along on arcuate path, being a rigid member of arcuate shape, or at least partly constructed from a flexible material.

Any suitable means, such as friction, spring pressure, a spring catch, or magnetic force, may be employed to retain the movable connector part in its position of engagement with the other connector part.

In the case of a socket and limb connector, the slidable part is preferably the limb part and such a slidable limb part may be operated in diverse ways. Examples of suitable operating arrangements include projections extending from the limb part beyond the pontic through a suitable hole or slot so as to be operable to engage or disengage the limb from the socket. Such projections may have holding extensions to make them easier to manipulate and they may also have covers to help prevent the access hole in the pontic filling with debris.

Magnetic force may also be used to move a movable connector part made of magnetisable material. In one embodiment, an operating tool could be magnetically coupled to the movable connector part, so that by subsequently manipulating the tool the required movement can be transmitted to the movable connector part.

Another possible operating arrangement involves the application of pressure to a flexible or mobile part of the surface of the pontic, such pressure being translated into the required movement of the connector part, either directly or by way of linkage.

A further possibility for actuating a movable connector part is the use of hydraulic pressure, advantages of which include the possibility of applying pressure remote from the movable connector part to be actuated and the possibility of simultaneously operating a plurality of movable connector parts in the same prosthetic construction.

Conveniently, a movable limb of a socket and limb connector is movable by means of a tool mechanically engaging the limb part. For instance, the limb part may be provided with indentations or projections with which the tool is engageable. In such embodiments, slots or notches may be provided to the guide tool into correct engagement with the limb part.

Locating devices may be provided to help align a limb part with its respective socket during installation and also to align a tool with an appropriate portion of the limb part during removal of the prosthetic construction.

The socket parts of a socket and limb connector may have suitable cross-sectional shape, such as more or less rectangular or triangular shapes, which may be best suited to posterior teeth and incisor teeth respectively.

In order that the invention may be readily understood, embodiments thereof will now be described, by way of example, with reference to the accompanying drawings, in which:

FIG. 7 is a plan view, with a top wall of the socket part removed, of the bridge connector shown in FIG. 6;

FIG. 8 is a cross-sectional view of the connectro taken on line X—X of FIG. 6.

FIG. 9 is a view looking along the axis towards a socket part of another embodiment of a socket and limb connector for a dental prosthetic construction, the socket part being shown in postion on an abutment tooth prior to embedding in filler material;

FIG. 10 is a side view of the FIG. 9 arrangement, with part of the tooth and a sidewall of the socket removed;

FIG. 11 is plan view of the FIG. 9 arrangement, with a top wall of the socket removed;

FIG. 21 is a transverse section on the plane E—E of the pontic illustrated in FIG. 12;

FIG. 22 is a transverse section of a pontic having a locating device received thereon and a limb-moving tool in position;

FIG. 23 is a horizontal section showing a bridge similar to that of FIG. 18, with a locating device and limb-moving tools in position, the limb parts of the connectors being engaged with the respective sockets;

FIG. 24 is a similar view to FIG. 23, but with the limb parts of the connectors disengaged from their respective sockets;

FIG. 27 is a side view of part of a denture and the adjacent teeth, the denture containing a connector;

FIG. 28 is a sectional view on the line F—F;

FIG. 29 is a sectional view on the line G—G; and

FIG. 30 is a sectional view on the line H—H.

Figure 1:
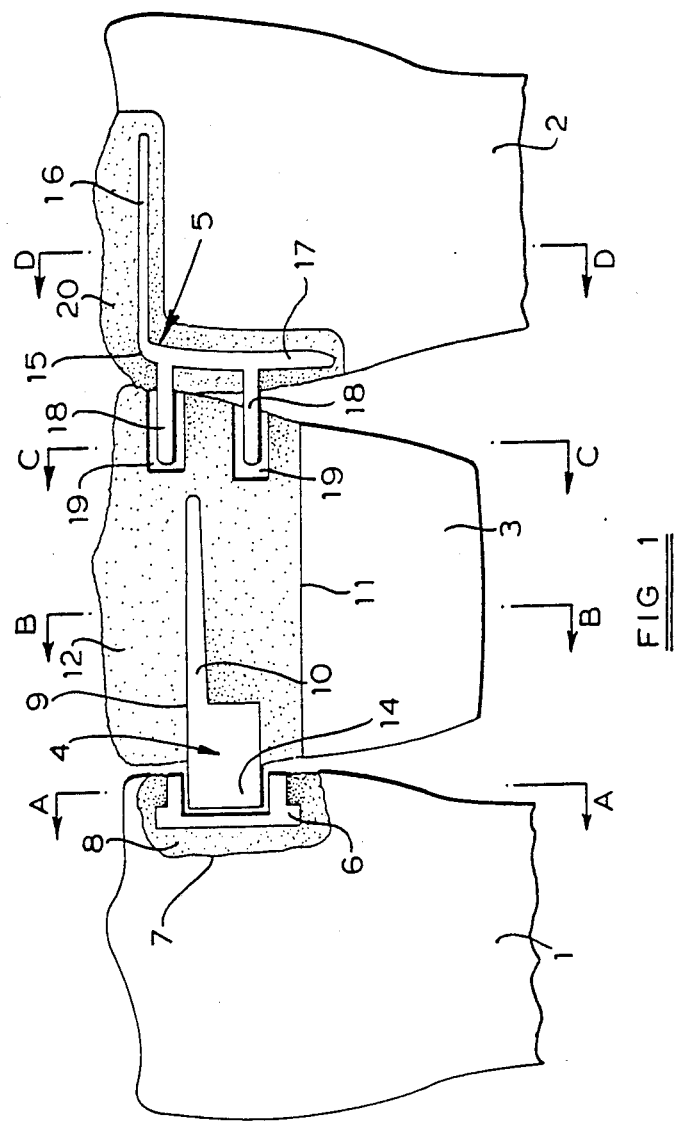
FIG. 1 is a schematic longitudinal section through a pair of prepared abutment teeth supporting an installed dental bridge construction embodying the present invention.
Figure 2:
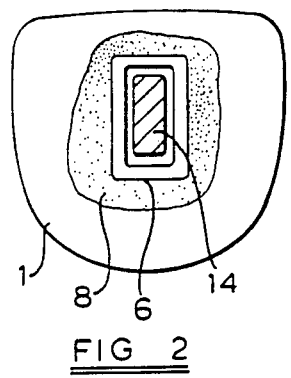
FIG. 2 is a transverse cross-section through one of the abutment teeth on the line A—A in FIG. 1.
Figure 3:
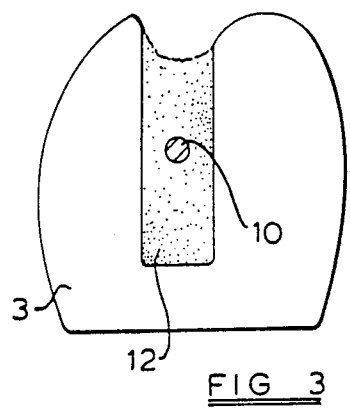
FIG. 3 is a transverse cross-sectional view through the artificial tooth or pontic of the bridge construction of the line B—B in FIG. 1.
Figure 4:
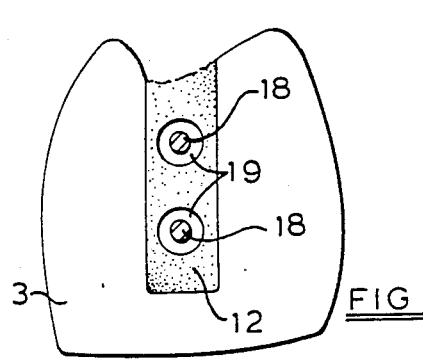
FIG. 4 is a transverse cross-sectional view through the pontic on the line C—C in FIG. 1.
Figure 5:
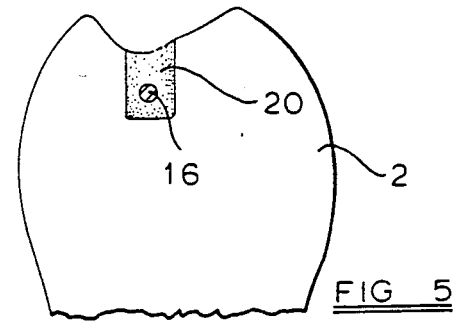
FIG. 5 is a transverse cross-sectional view through the other abutment tooth on the line D—D in FIG. 1.

Referring now to the drawings, FIG. 1 shows a fixed dental bridge construction embodying the present invention, in which an artificial tooth or pontic 3 is supported in a gap between two abutment teeth 1 and 2 by respective bridge connectors 4 and 5.

The bridge connector 4 is shown schematically in FIG. 1 as comprising a first or socket part 6 which is embedded in a matrix of filler material 8 received in a prepared, oversized and under-cut cavity 7 formed in a vertical surface of the abutment tooth 1. A second or limb part 9 of the connector 4 has a portion 10 at one end thereof received in a fixing cavity in the form of a slot 11 formed in the pontic 3, the said portion 10 being embedded in a matrix of filler material 12. A projecting joint portion 14 at the other end of the limb part 9 projects from the filler material 12 and fits into the socket part 6 with sufficient play to enable relative movement of the pontic 3 relative to the abutment tooth 1 for stress-breaking purposes.

The bridge connector 5 is a unitary structure and consists of a dihedral strip 15 having a horizontal arm 16 and a vertical arm 17. The strip 15 fits into an L-shaped surface groove or cavity cut for this purpose in adjacent horizontal and vertical surfaces of the abutment tooth 2. Fingers 18 formed integrally with the arm 17 of the strip 15 project into the slot of the pontic 3 where they are embedded in the matrix of filler material 20 filling the slot. Each of the fingers 18 is covered with a layer of resilient material 19 which permits limited stress-breaking movements of the pontic 3 relative to the abutment tooth 2.

Figure 6:
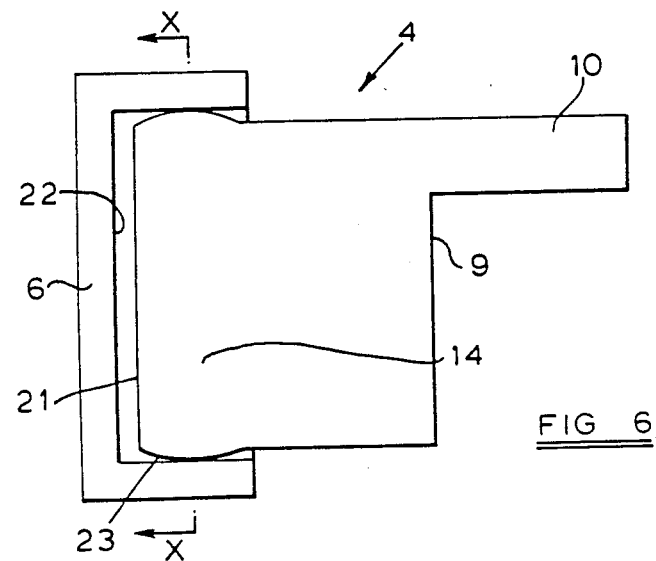
FIG. 6 is a side view, with one side wall of a socket part removed, of bridge connector structure for a dental bridge construction embodying the invention.

FIGS. 6 to 8 show on example of a configuration which may be adopted in the case of the bridge connector 4. As shown in these Figures, the limb part 9 of the connector 4 for embedding in the matrix of filler material 12 in the slot 11 of the pontic 3 may have its projecting joint portion 14 fitting quite snugly into the socket part 9 in the abutment tooth with a flat end surface 21 of the joint portion 14 spaced from the floor 22 of the socket part 6. The bearing surfaces 23, 24 of the joint portion 14 within the socket part 6 are rounded to form a kind of universal joint, permitting stress-breaking movement of the pontic 3 in the required directions, including longitudinally of the limb part 9, but precluding rotation around the longitudinal axis.

In some circumstances it may be desirable to provide a construction which permits rotational movement on one side. In this case, one connector could be constructed as illustrated in FIGS. 6 to 8 and the other connector could be of similar form but modified to permit such rotation about the longitudinal axis.

The bridge connector components can be standard items made of any suitable material, such as stainless steel or titanium or a composition including carbon fibres. The pontic may be made of dental metal or a non-metallic dental material. Those parts of a connector component which are to be covered by the filler material may also be treated, for example by having the surface thereof roughened, so as to make the filler material adher to the component.

The filler material used to fill the cavities in the abutment teeth and the pontic, and thus attach the component to the tooth or pontic, may be any suitable material, such as a composite dental filling material.

Whilst, in the above described embodiment, the connectors 4 and 5 are embedded in filler material in cavities in the abutment teeth and the pontic, it is envisaged that, in appropriate cases, a connector embodying invention could be attached entirely or in part to a prepared surface of an abutment tooth. In such a case, a procedure such as acid etching may be used to prepare the surfaces of the tooth and connector to be attached to one another by filler material or the like placed between the surfaces.

It is envisaged that a range of different types and sizes of standard bridge connectors may be provided for different circumstances and a range of pontics may also be provided with suitable fixing cavities for use with the various connectors.

In providing a patient with a dental bridge construction as hereinbefore described, a dental procedure is first carried out to prepare the abutment teeth by forming the required cavities or otherwise preparing the surface of the tooth to receive the standard bridge connectors selected for the particular construction involved.

The bride construction is then installed by attaching the corresponding bridge connectors to the abutment teeth using the filler material, introducing the relevant portions of the bridge connectors into the groove of a suitable standard or custom-made pontic and thereafter fillng the groove in the pontic with a matrix of filler material to embed and retain the connector.

The advantages of the proposed bridge construction are seen in the fact that the bridge connectors can be ready made components which are not intended to fit accurately either the abutment tooth or the artificial tooth. Consequently, high precision laboratory work is eliminated and the dental preparation work to enable the construction of such a bridge is simplified and does not involve carrying out radical and accurate surgery on the healthy abutment teeth.

The proposed bridge construction also allows a bridge connector to be so arranged that the path of withdrawal of the connector, or separation of its parts, is transverse to the forces encountered in the mouth, thereby reducing the chances of the pontic becoming detached from the abutment teeth. This construction further permits effective stress-breaking structures to be incorporated into the bridge with consequent reduction in the likelihood that the bridge will break. Moreover, the forces encountered in the mouth will not subject the bridge construction to shearing forces tending to break the connection between the bridge construction and abutment teeth as in the prior art, but will subject the structure to more readily resisted compression forces.

Whilst the above embodiment of the invention has been described with reference to fixed dental bridges, it is envisaged that, connectors embodying the invention could be used as denture retainers, provided a two-part connector structure is employed and the coupling of the connector parts is effected in a direction transverse to the forces encountered in the mouth. For example, the connector of FIGS. 6 to 8 is thought to be specially suitable for use in the case where a denture is to be provided to replace teeth at the back of the mouth behind sound front teeth to which a connection can be made.

FIGS. 9 to 11 show another embodiment of a socket part of a socket and limb connector for use in attaching a pontic to an abutment tooth. The socket part comprises a socket 31 attached to a perforated base plate 32 from which extend upper substantially horizontal limbs 33 which have an arcuate configuration in the horizontal plane. To attach the socket part to an abutment tooth 35, the socket part is positioned in an oversized cavity in the tooth 35 and the remaining space 34 is later filled with a suitable material. Part of the socket may protrude from the left side wall of the tooth. Such a means of attaching the socket part and abutment tooth enables the socket part to occupy a cavity resulting from the removal of a pre-existing mesio-occlusal or disto-occlusal filling, whilst at the same time acting as a reinforcement for the matrix of filler material.

Figures 12, 13:
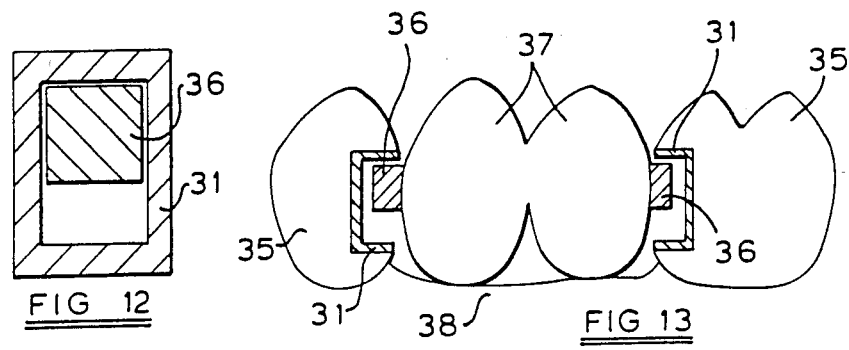
FIG. 12 is a transverse section through a socket and limb connector which allows vertical movement.
FIG. 13 is a side view of a fixed dental bridge mounted between abutment teeth by socket and limb connectors which allow vertical movement, part of the abutment teeth and sidewalls of the sockets having been removed and the pontics being in the resting position.

FIG. 12 illustrates diagrammatically how a joint part of a limb 36 of the connector may be afforded limited vertical movement within the socket 31. In FIG. 12, the limb 36 is shown near the upper limit of its permitted vertical movement.

Figure 14:
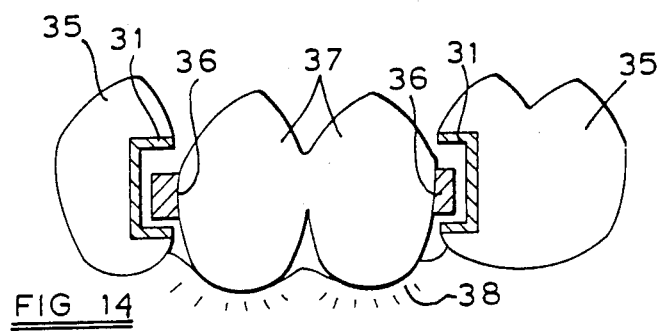
FIG. 14 is a similar view to FIG. 13, but with the pontics subjected to an occlusal force.

The dental bridge construction shown in FIG. 13 comprises a pair of integrally formed pontics 37 each connected to a respective abutment tooth 35 by means of a respective connector consisting of a socket 31 and a limb 36, such that limited vertical moement of the pontics 37 is permitted. In the upper resting position shown in FIG. 13, the gum 38 is in light contact with the pontics but is uncompressed. FIG. 14 shows the bridge of FIG. 13 when subjected to an occlusal load. In this state, the pontics have moved vertically downward a little, with coresponding movement of the limbs 36 within the sockets 31. The gum 38 has been compressed and is providing resistance to the occlusal force. This type of arrangement would be advantageous in those instances in which it is desirable to reduce the forces transmitted to an abutment tooth by a pontic.

Figure 15:
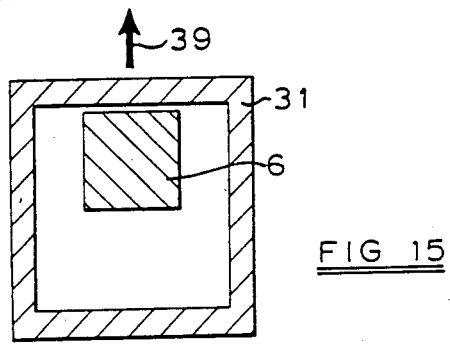
FIG. 15 is a transverse section through a socket and limb connector which allows for both vertical and horizontal movement.

As shown diagrammatically in FIG. 15, a limb 36 of a socket and limb connector may be permitted both vertical and horizontal movment. FIG. 15 shows such an arrangement with the limb 36 positioned at the upper limit of vertical movement within the socket part 31 and near the centre of its range of horizontal movement. Such a connector transmits a minimum of chewing forces from the pontic to the abutment teeth, provided that the pontic is adequately supported by either the gum or other teeth. Movement of the pontic is an occlusal direction (arrow 39) is prevented, so that the pontic is held in position in the mouth. Such a connector arrangement would be a especially useful in the case of a partial denture coupled to weak or loose natural teeth.

Figure 16:
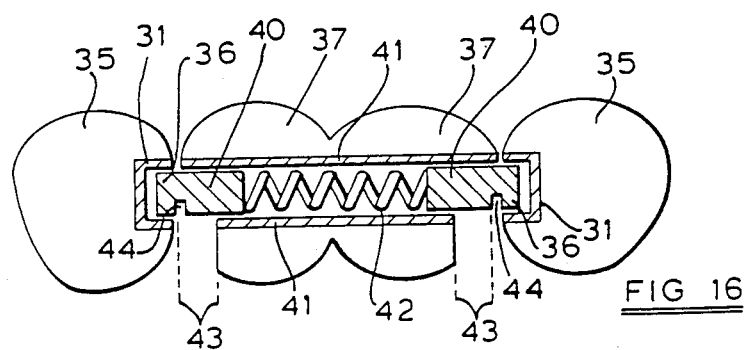
FIG. 16 is a horizontal section through a removable dental bridge attached to abutment teeth by socket and limb connectors having straight limb parts, the limb parts being shown in their socket-engaging positions.

The removable bridge construction shown in FIG. 16 comprises a pair of integrally formed pontics 37 through which extends a horizontal sleeve 41 containing freely slidable connector limb parts 40. A spring 42 disposed between the limbs 40 biases the limbs apart into engagement with the respective socket parts 31.

Figure 17:
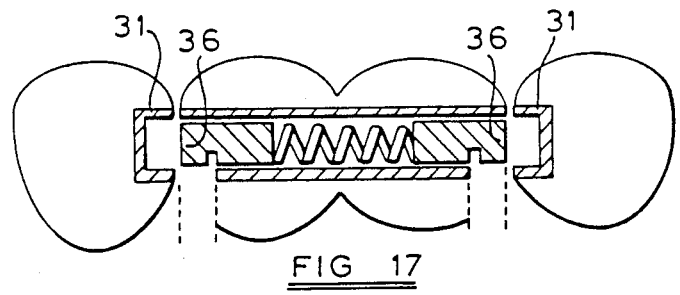
FIG. 17 is a similar view to FIG. 16, but with the limb parts of the connectors disengaged from their respective sockets.

The limbs 40 are formed with notches 44 with which a tool may be engaged through slots extending through both the pontic and sleeve, and indicated by dotted lines 43, in order to move the limbs to a retracted position in which they are disengaged from the sockets 31 as shown in FIG. 17. With the limbs thus withdrawn from the sockets, the pontics are no longer attached to the abutment teeth and the bridge may thus be removed from the mouth. A removable bridge has a number of advantages when compared to a fixed one, including simplified hygiene procedures for the wearer, as well as improved access for the dentist for inspection and maintenance.

Figure 18:
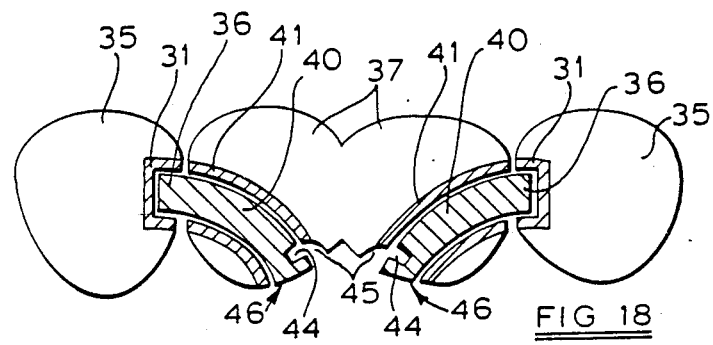
FIG. 18 is a horizontal section through a removable dental bridge which is mounted between abutment teeth by two socket and limb connectors with curved limb parts, the bridge being shown with the limb parts engaged with the respective socket parts in the abutment teeth.

As shown in FIG. 18, the limbs 40 may have an arcuate shape and be received in respective sleeves 41 in the pontics 37. The end 46 of the limbs furthest from the joint part 36 are more or less flush with the palatal surface of the pontics 37. Notches 45 in the pontics facilitate engagement of an actuating tool in notches 44 in the limbs.

Figure 19:
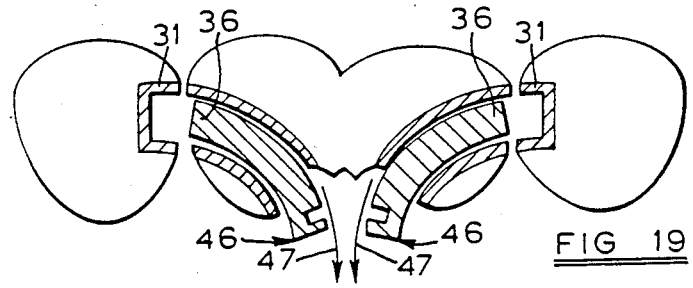
FIG. 19 is a similar view to FIG. 18, but with the limb parts of the connectors disengaged from their respective sockets.

Arrows 47 in FIG. 19 illustrate the direction of the force applied to retract the limbs from the sockets in the FIG. 18 embodiment. In this retracted condition of the limbs, the ends 46 now protrude from the surface of the pontics. Re-engagement of the limbs with the sockets 31 may be achieved either using a tool or by pressure on the ends 46 following alignment of the joint part 36 with the socket parts 31.

A curved connector limb has an advantage in that the end furthest from the joint may be situated at the surface of the pontic facing the tongue, cheek or chewing surface, where it is readily accessible.

Figure 20:
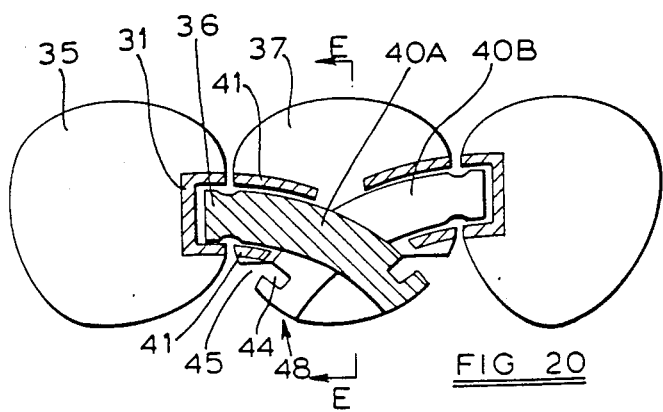
FIG. 20 is a plan view of a small removable dental bridge supported between two abutment teeth by limb and socket connectors having curved limb parts, portions of the teeth and the top walls of the socket being removed to show the limb parts.

FIG. 20 illustrates how two curved connector limbs 40A and 40B may be accomodated in different planes in respective sleeves 41 within the same narrow pontic. The sleeve 41 are confined to short lengths guiding the limb close to the joint portions thereof, the remainder of the limbs sliding within a tunnel formed by the matrix of filler material 34. FIG. 21 shows the limbs 40A and 40B in the region where they are simply placed in filler material. There is sufficient latitude between the materials of the connector limb and the filler material to allow the connector limb to slide.

End stops (not illustrated) may be provided in order to prevent movement of a sliding connector limb beyond determined limits, which would normally be fully engaged and fully retracted positions.

FIGS. 22, 23 and 24 illustrate the use of a locating device for aligning pontics relative to abutment teeth and for assisting in the manipulation of sliding connector limbs. This locating device takes form of a cap 48 constructed so as to be a tight fit over the pontics, abutments and as much of the dental arch as desired or necessary. Like a common type of sportsman gun shield, the cap 48 is designed to engage undercuts and so to stay firmly in place following insertion. However, the cap is constructed of a material which is sufficiently flexible to allow the device to be removed and reinseted fairly easily. Actuating rods 49 are positioned so that, during insertion of the cap they will slide along grooves 45 in the pontic so as to be guided into notches 44 in the bolts, clearing away any food debris in the process, so that, when the cap is fully located, the rods 49 will be engaged in the notches 44. In order to insert a removable bridge using the described locating device, the connector limbs are moved into the extended socket-engaging position and the bridge is placed fully into its location in the cap. The rods 49 are now used to slide each bolt into the retracted position, the movement of the rods and connector limbs being made possible by the flexible nature of the cap material. The cap 48 containing the bridge is now inserted into the mouth and slipped into position. The pontics are thus correctly aligned with the abutment teeth and the limbscan be moved to the extended position so as to enter the socket parts of the connectors in the abutment teeth, following which the cap 48 can be removed, leaving the bridge in position. The above procedure may be reversed in order to remove the bridge.

It is envisaged that, in some embodiments of the cap 48, a space may be provided into which the ends 46 of the connector limbs can move during retraction without them having to distort the cap (see FIG. 24).

Caps used as aids in positioning pontics and operating devices for connector limbs need not be flexible. If made of a rigid material, such as acrylic resin, they may be designed to avoid undercuts to the path of insertion, whilst at the same time conforming to sufficient of the surfacs of both the natural and artificial teeth to make location of a prosthetic construction easy and accurate. In the case of such rigid caps, springs or other catches may be fitted to engage undercuts both in the natural dentition and in the pontics in order to help keep the cap in place during operation of a sliding connector limb and also to hold the prosthetic construction in the cap during insertion or removal from the mouth.

A connector limb operating rod attached to a cap may be designed to engage the appropriate parts of the limb during insertion of the cap. However, in a preferred arrangement, the pontic is first fully inserted into the cap. Subsequent operation of a mechanism first engages the rod and then moves it in order to operate the sliding connector limb. Such a sequential movement may be readily achieved by means of levers, incline planes, cams and the like. Preferably, an operating lever would be arranged to project from the mouth so as to be easily manipulated, possibly in conjunction with a second reciprocal lever which could further simplify use. One or other of the operations of engaging or retracting the sliding limbs may be spring-assisted.

Figure 25:
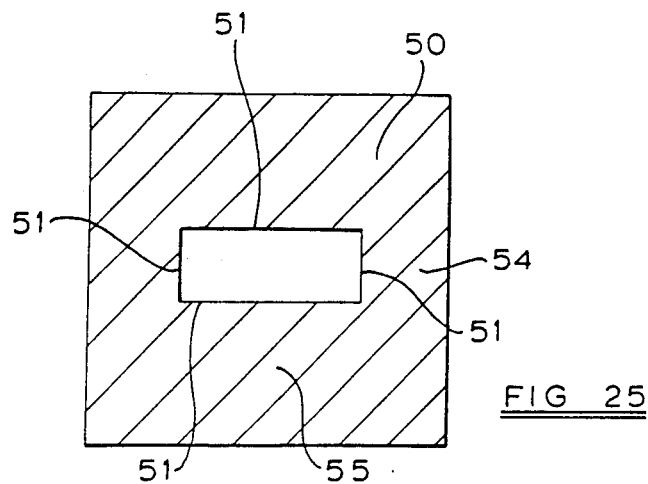
FIG. 25 is a front view of a socket part of a socket and limb connector in accordance with another embodiment of the invention.
Figure 26:
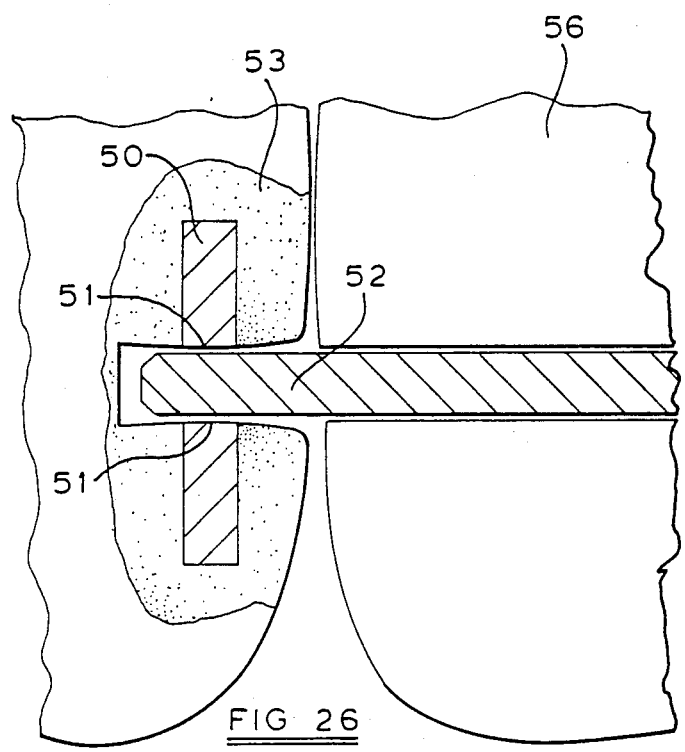
FIG. 26 is a partial vertical cross-sectional view of a prosthetic dental construction employing a connector having a socket part of the form shown in FIG. 25.

Referring now to FIGS. 25 and 26 of the drawings, which illustrate a particularly simple embodiment of the present invention, it will be seen that a socket part 50 of a connector for a dental prosthetic construction is fashioned from a sheet of material by forming a substantially rectangular aperture adapted to receive a connector limb 52 as shown in FIG. 26. The edges 51 of the aperture which are to support the limb 52 may be shaped, if desired, to allow for both a snug fit of the limb and limited stress-breaking movements. The socket is embedded in a matrix of filler material 53 and those surfaces of the socket part which are to contact the filler material 53 may be treated to provide good adhesion. The connector limb 52 partially within the pontic 56, has a parallel-sided portion where it passes through the aperture of the socket part, the required limited stress-breaking movements in this case being provided by the shape of the socket, rather than that of the bolt.

The illustrated socket part 50 has an essentially rectangular cross-section. This may be positioned in any convenient plane. For example, in posterior teeth, the longer side of the pocket aperture would be horizontal, as illustrated. When used for incisor teeth, a more vertical arrangement may be advantageous.

In some embodiments of the present invention, all or parts of a connector socket may be constructed of filler material. For example, the side wall 54 or 55 could be omitted.

It will be appreciated that the movements which need to be permitted between the socket and limb parts of a connector are very small and it is envisaged that such connectors may be supplied with the limb as a tight fit within the socket, the required freedom of movement to suit any given circumstances then being introduced by carrying out modification of the connector parts, such as by grinding or the like, at the time of installation.

The limb and socket connectors described above are mainly intended to connect artificial teeth to adjacent natural ones. However, when dentures ae to be constructed it is common practice to anchor artificial teeth to natural ones which may be some distance from the gap—the intervening space being spanned by a plate or a bar. Clasps and rests are commonly used for attachment but have many disadvantages. Limb and socket connectors could be used in many of these situations, the sockets being oriented with the long axis more or less parallel with the plane of the dental arch and facing a convenient direction—for instance, towards the palate. It is envisaged that the limbs would be mounted on movable arms—or the like—to enable engagement of the limbs and sockets. One such embodiment will now be described, by way of example, with reference to FIGS. 27 to 30 of the drawings.

The mechanism is based on a connector limb attached to a kinged arm which is spring loaded to keep it in its correct (closed) position. Large components of the forces imposed on the limb from the denture are transmitted through the surfaces of the arm adjacent to denture material, rather than through the hinges. The arm is extended beyond the hinges for ease of spring application and operation.

Referring now to FIGS. 27 to 30, the connector has an arm 101 which in this case is "L" shaped, and fits loosely into a correspondingly shaped slot in the denture 102. Hinge-like projections 103 from the arm fit into depressions 104 (FIG. 30) in the dental material. Further hinge-like projections 105 fit depressions 106 on the inner aspect of the denture. The position of hinges 103 and 105 which are out of the section in FIG. 29 are indicated by dotted lines, as is the hinge 105 which is out of sight in FIG. 27. Rests 107 project from arm 101 and fit depression 108 in the denture material. In FIG. 28 the connector limb 109 can be seen engaged in a socket 110 of the natural tooth 111. A part of the arm 101 on the opposite side of the hinges to the connector limb is made of a spring material 112 and, for ease of operation, is bowed so as to project in part above the surface of the denture material. The end 113 of the spring rests on a platform 114 of the denture. Spring tension is adjusted so that the spring end 113, hinges 105 and rests 107 are held in contact with the corresponding parts of the denture. When the denture is in position the connector limb 109 is engaged in the socket 110. In order to withdraw the limb from the socket, pressure—for instance finger pressure)—may be applied to the bowed part of the spring 112 in the direction of the arrow 115 (FIG. 29). This would bend the spring, causing the arm 101 to pivot on hinges 103, thus moving the limb out of the socket.

The embodiment of FIGS. 27 to 30 would be extremely simple to incorporate into a denture. It is envisaged that a range of standardised shapes and sizes of the arm with its projections would be produced together with aids to enable the necessary slots and depressions to be easily incorporated into the denture when it is made.

Whilst the above described embodiments of the invention employ abutment tooth socket defined by connector parts, it is envisaged that all or part of such sockets could be fashioned as suitably prepared cavities in the substance of the abutment tooth or in a matrix of filler material.

In those instances when it is desired to fit a slidable connector limb to a pontic in the laboratory, the socket part may be fitted to its abutment tooth either before or after the pontic is constructed.

When a socket has been fitted first one way making a pontic with its connector limb in the correct position is as follows:

A curved connector limb is fitted into the socket and held steady while being embedded in a small mass of impression material, such as a rubber base material, about the size of the pontic but without undercuts to the line of withdrawal, and with the material flush with the 'working end' of the connector limb. After this has set, a second impression, of a type which will not adhere to the first, it taken over the top of it to include the abutment teeth. When set this is removed. The first impression will be left behind, anchored by the enclosed connector limb. The connector limb is now withdrawn a little way through the first impression material in order to disengage it from a socket, when the first impression may be removed from the mouth. The connector limb is now pushed back into its original position in the impression material and the first impression is replaced into its correct position within the second impression. A model prepared from this composite impression will have the connector limb embedded in it its correct location in the model abutment tooth. Following withdrawal of the connector limb from the model this, in turn, will have a correctly located socket.

It is envisaged that a series of aids would be provided to assist in the construction of sockets. They may be made of a translucent material to facilitate the use of light-cured filler matrix material such as 'composite' materials. It is envisaged that these aids would include gauges to define the minimum size and depth of a cavity, formers to compact and shape the filler matrix deep into the socket part, and aids to both hold the socket part steady while the surrounding matrix was inserted and also correctly shape the matrix.

In addition, a range of burrs with shoulders may be provided as a help to achieving correct cavity depth. also suitable curved connector limbs and sockets may be provided for the construction of models as previously described.

Any of the connector parts may be suitably coloured—for instance, tooth or gum coloured.

What is claimed is:

1. A dental prosthetic construction comprising a pontic and a connector limb attached to the pontic, the connector limb having a joint portion received in a socket of an abutment tooth to retain the pontic in an intended position, the joint portion of the connector limb having curved bearing surfaces which engage flat bearing surfaces in the socket, the joint portion of the connector limb being introduced into the socket in the abutment tooth along a path of insertion which is substantially parallel to the dental arch containing the abutment tooth and having bearing surfaces engaging bearing surfaces in the socket such that there is limited freedom of angular movement of the connector limb about the joint portion so as to permit stress-breaking relative movement between the connector limb and socket whilst maintaining contact between the connector limb and socket.

2. A dental prosthetic construction comprising a pontic and a connector limb attached to the pontic, the connector limb having a joint portion received in a socket of an abutment tooth to retain the pontic in an intended position, the joint portion of the connector limb having flat bearing surfaces which engage curved bearing surfaces in the socket, the joint portion of the connector limb being introduced into the socket in the abutment tooth along a path of insertion which is substantially parallel to the dental arch containing the abutment tooth and having bearing surfaces engaging bearing surfaces in the socket such that there is limited freedom of angular movement of the connector limb about the joint portion so as to permit stress-breaking relative movement between the connector limb and socket whilst maintaining contact between the connector limb and socket.

* * * * *